United States Patent
Naughton et al.

(12)

(10) Patent No.: US 6,599,721 B2
(45) Date of Patent: Jul. 29, 2003

(54) PROCESS FOR PREPARING OPTICALLY ACTIVE 3,3,3-TRIFLUOROMETHYL-2-ALKYLPROPIONIC ACID DERIVATIVES

(75) Inventors: Andrew Naughton, Gipf-Oberfrick (CH); Nicholas Shaw, Visp (CH)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 09/938,333

(22) Filed: Aug. 23, 2001

(65) Prior Publication Data

US 2002/0039769 A1 Apr. 4, 2002

Related U.S. Application Data

(63) Continuation of application No. PCT/EP00/01491, filed on Feb. 23, 2000.

(30) Foreign Application Priority Data

Feb. 23, 1999 (EP) ............................................. 99103420

(51) Int. Cl.⁷ .......................... C12P 13/02; C12P 7/40; C12P 7/42
(52) U.S. Cl. ....................... 435/129; 435/136; 435/146; 435/280
(58) Field of Search ............................... 435/136, 146, 435/280, 129

(56) References Cited

U.S. PATENT DOCUMENTS 4,895,588 A    1/1990   Dingwall ...................... 71/92

FOREIGN PATENT DOCUMENTS

| DE | 19725802    | 1/1998 | ......... C07C/59/115 |
| EP | 0298029     | 6/1988 | ......... C07D/401/04 |
| EP | 0524781     | 7/1992 | ......... C07D/213/75 |
| WO | WO 98/01568 | 6/1996 | ............ C12N/15/55 |
| WO | 9801568     | 1/1998 | ............ C12N/15/55 |
| WO | 9904028     | 1/1999 | ............ C12P/41/00 |

OTHER PUBLICATIONS

Kurt Konigsberger et al., "The synthesis of (R)–and (S)–alpha–trifluoromethyl–alpha–hydroxcarboxylic acids via enzymatic resolutions" Tetrahedron: Asymmetry, Bd. 10, Nr. 4, Feb. 26, 1999, Seiten 679–687, XP002150873 Schema 1.

Primary Examiner—Herbert J. Lilling
(74) Attorney, Agent, or Firm—Darby & Darby

(57) ABSTRACT

The invention relates to a novel method for the preparation of optically active 3,3,3-trifluoromethyl-2-alkyl propionic acid derivatives of the general formulae (I) and (II), in which R is ethyl or methyl and X is OH or $NH_2$, provided that if R is methyl X≠—OH. The method comprises the reaction of a racemic propionic acid amide of the general formula (III) either by means of microorganisms which are able to use the propionic acid amide in the form of the racemate or one of its optically active isomers as the only nitrogen source or by means of a polypeptide with amidohydrolase activity which is able to hydrolyze the propionic acid amide. The invention also relates to new optically active representatives of this category of compounds.

9 Claims, 1 Drawing Sheet

Figure 1:
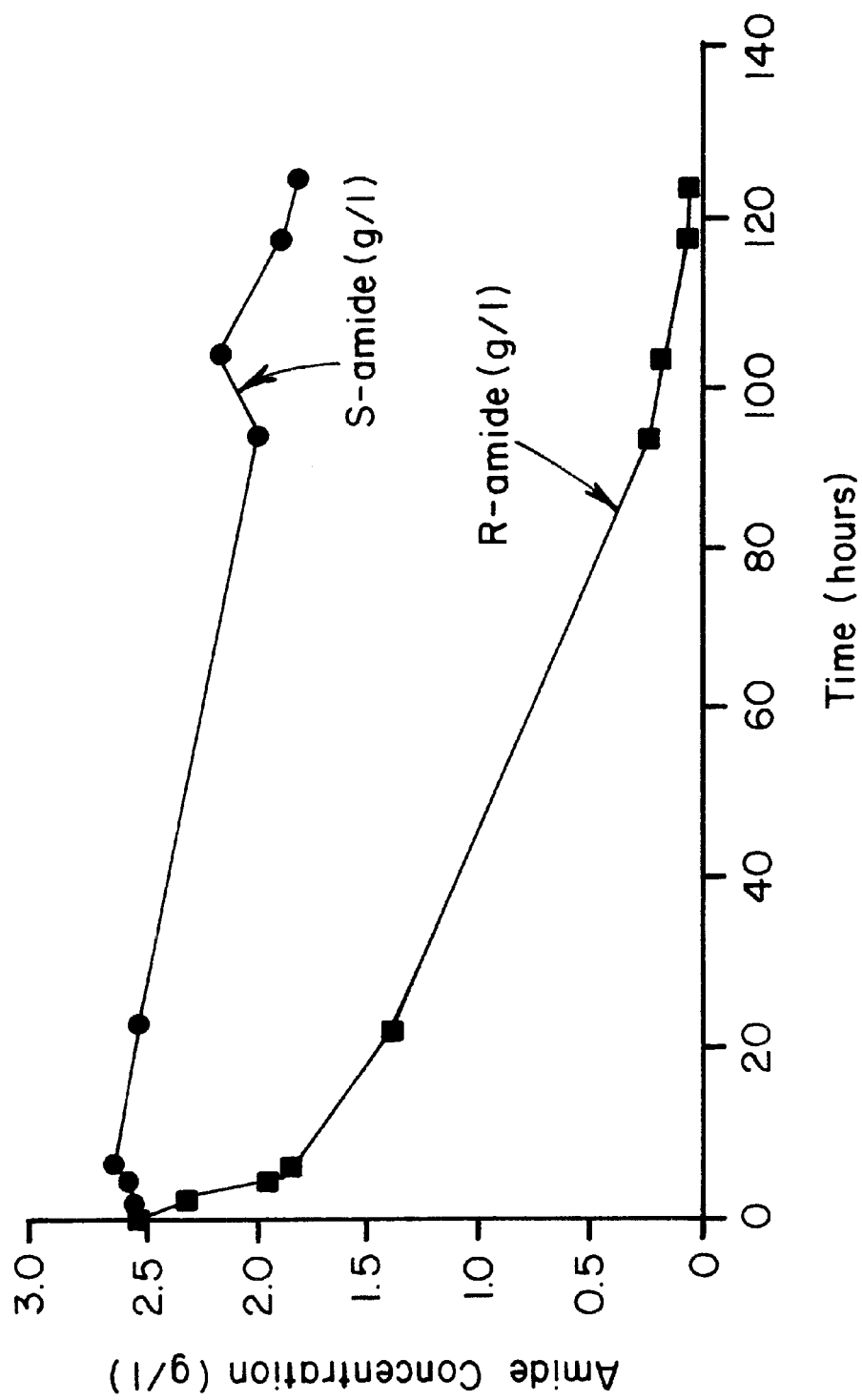

PROCESS FOR PREPARING OPTICALLY ACTIVE 3,3,3-TRIFLUOROMETHYL-2-ALKYLPROPIONIC ACID DERIVATIVES

This is a continuation of International Application Serial No. PCT/EP00/01491, filed Feb. 23, 2000, the entire disclosure of which is hereby incorporated by reference.

The present invention relates to a novel process for preparing optically active 3,3,3-trifluoro-2-alkylpropionic acid derivatives of the general formulae

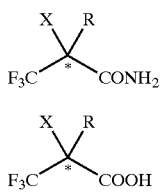

and to novel representatives of this compound class.

Up until now, the known 3,3,3-trifluoro-2-alkylpropionic acid derivatives, such as 3,3,3-trifluoro-2-amino-2-methylpropionic acid, have been synthesized using an amino acylase and starting from racemic trifluoroacetyl-R(+)2-trifluoromethylalanine. The product is only formed in low yield in this method.

3,3,3-Trifluoro-2-alkylpropionic acid derivatives, such as 3,3,3-trifluoro-2-hydroxy-2-ethylpropionic acid, are important intermediates for preparing therapeutic amides (EP-A 0 524 781).

Up until now, the known 3,3,3-trifluoromethyl-2-alkylpropionic acid derivatives, such as 3,3,3-trifluoro-2-amino-2-methylpropionic acid, have been synthesized using an amino acylase and starting from racemic trifluoroacetyl-R(+)2-trifluoromethylalanine. The product is only formed in low yield in this method.

The object of the present invention was to make available a process for preparing optically active 3,3,3-trifluoro-2-alkylpropionic acid derivatives in which the desired products are formed both in excellent yield and in relatively short reaction times.

This object is achieved by the process as claimed in claim 1.

According to the invention, the 3,3,3-trifluoro-2-alkylpropionic acid derivatives are prepared by transforming a racemic 3,3,3-trifluoro-2-alkylpropionamide of the formula

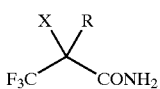

in which R denotes ethyl or methyl and X denotes —OH or NH$_2$, with the exception that, when R=methyl, X≠OH, either using microorganisms which are capable of utilizing the latter, as their sole source of nitrogen, in the form of the racemate or of one of its optically active isomers, or using a polypeptide which possesses amidohydrolase activity and which is capable of hydrolyzing the latter.

The starting compounds, i.e. the 3,3,3-trifluoro-2-alkylpropionamides of the general formula III, can be prepared using customary chemical methods. The starting compounds, such as 3,3,3-trifluoro-2-hydroxy-2-ethylpropionamide, are preferably prepared from the corresponding 3,3,3-trifluoro-2-alkylpropiononitrile of the general formula

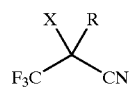

in which R and X have said meaning, by hydrolyzing it with a mineral acid.

The mineral acid which is used can be one which is customary for the skilled person, for example phosphoric acid, hydrochloric acid or sulfuric acid. The mineral acid which is used is preferably sulfuric acid. The mineral acid is expediently employed in excess, preferably in a quantity of from 2 to 4 mol per mole of propiononitrile.

The hydrolysis is expediently carried out at a temperature of from 20 to 140° C., preferably of from 90 to 120° C.

All the microorganisms which are capable of utilizing, as their sole source of nitrogen, the propionamide of the formula III in the form of the racemate or of one of its optically active isomers, and also all the isolated polypeptides which possess amidohydrolase activity and which are capable of hydrolyzing the propionamide of the formula III, can be used for the biotransformation according to the invention.

Microorganisms, and polypeptides having amidohydrolase activity, which possess this property, and also the isolated and sequenced DNA fragment which encodes the amidohydrolase are already known and described in WO 98/01568. The microorganisms which can be employed are both what are termed the "wild-type strains", which can be isolated from soil samples, sludge or effluent, as described in WO 98/01568, or what are termed "recombinantly altered microorganisms", which are transformed with the isolated DNA fragment, as described in the WO. The biotransformation is expediently carried out using microorganisms of the genus Klebsiella or using "recombinantly altered microorganisms". The microorganisms of the genus Klebsiella which are preferably employed are those of the species *Klebsiella oxytoca* PRSI (DSM 11009), *Klebsiella oxytoca* PRSIK17 (DSM 11623), *Klebsiella panticula* ID-624 (DSM 11354) or *Klebsiella pneumoniae* ID-625 (DSM 11355) or their functionally equivalent variants and mutants. Examples of suitable "recombinantly altered microorganisms" are microorganisms of the species *Escherichia coli* DH5 and *Escherichia coli* XL-1 Blue MRF, in each case harboring plasmid pPRS1b, pPRS2a (DSM 11635), pPRS4 or pPRS7. Preference is given to using *Escherichia coli* XL-1 Blue MRF harboring plasmid pPRS7. The microorganisms having the designation DSM 11009 were deposited in the Deutsche Sammlung von Mikroorganismen und Zellkulturen [German Collection of Microorganisms and Cell Cultures] GmbH, Mascheroderweg 1b, D-38124 Braunschweig, in accordance with the Budapest Treaty, on Jun. 24, 1996, while those having the designation DSM 11623 were deposited in this same institution, and in accordance with the Budapest Treaty, on Jun. 20, 1997, those having the designations DSM 11354 and DSM 11355 on Dec. 27, 1996 and those having the designation DSM 11635 on Jun. 30, 1997.

The biotransformation can be carried out using resting cells (cells which are not growing and which no longer require any C source or energy source) or using growing cells, after the microorganisms have been cultured in a customary manner. The biotransformation is preferably carried out using resting cells.

It is possible to employ media which are customary to the skilled person, such as low molecular weight phosphate buffer, HEPES buffer or mineral salt media, for the biotransformation.

The biotransformation is expediently carried out while adding the 3,3,3-trifluoro-2-alkylpropionamide of the formula III on one occasion or continuously such that its concentration does not exceed 10% by weight, preferably 2.5% by weight.

The pH of the medium can be in a range of from 4 to 12, preferably of from 5 to 11. Expediently, the biotransformation is carried out at a temperature of from 10 to 80° C., preferably of from 10 to 50° C.

After a customary transformation time of from 1 min to several days, the optically active 3,3,3-trifluoro-2-alkylpropionic acid derivatives of the general formulae I and II can then be isolated using customary working-up methods, such as extraction.

It was found that, when 3,3,3-trifluoro-2-amino-2-methylpropionamide is employed as the substrate, the corresponding R-acid is formed within 5 minutes and the corresponding S-amide can then be isolated.

The racemic 3,3,3-trifluoro-2-hydroxy-2-ethylpropionamide of the general formula III and the corresponding (+)-acid, the corresponding (−)-amide and the (S)-3,3,3-trifluoro-2-amino-2-methylpropionamide are all compounds which have not previously been described in the literature and consequently form part of the invention.

It was furthermore found that the optically active 3,3,3-trifluoro-2-alkylpropionamides of the general formula I can be hydrolyzed, in a known manner, into the optically active 3,3,3-trifluoro-2-alkylpropionic acid derivatives of the general formula II. In this connection, preference is given to hydrolyzing (S)-3,3,3-trifluoro-2-amino-2-methylpropionamide into (S)-3,3,3-trifluoromethyl-2-amino-2-methylpropionic acid.

The hydrolysis is effected in analogy with the hydrolysis described in WO 98/01568. This hydrolysis preferably takes place either chemically, in the presence of a base, or microbiologically, using microorganisms of the genus Rhodococcus.

EXAMPLE 1

Preparation of Optically Active 3,3,3-trifluoro-2-hydroxy-2-ethylpropionamide and of the Corresponding Optically Active Propionic Acid

1.1 Preparation of racemic 3,3,3-trifluoro-2-hydroxy-2-ethylpropionamide

Concentrated sulfuric acid (15.3 g) was added, under an argon atmosphere, to a 100 ml flask and the starting compound 3,3,3-trifluoro-2-hydroxy-2-ethylpropiononitrile (Fluorchem) (8 g) was then added dropwise. The reaction mixture was heated at 115° C. for 15 min and then cooled down to 8° C.; distilled water (21.8 g) was then added slowly. Diethyl ether was then added and the whole was stirred for 20 min.

After the phases had been separated, the ether phase was washed with water (25 ml), with aqueous saturated NaHCO$_3$ (25 ml) and once again with water (25 ml), then collected, dried over Na$_2$SO$_4$, filtered and dried in vacuo. The resulting oil was treated with n-hexane and stirred overnight. A total of 4.27 g of dried crystals, corresponding to a yield of 48%, was obtained.

1.2 Biotransformation

*E. coli* XL-1-Blue MRF/pPRS7 cells were grown in NYB (Nutrient Yeast Broth) medium containing 100 μg of ampicillin/ml up to an optical density of OD$_{650}$=4.74. The cells were then washed in 100 mM phosphate buffer (pH 8.0). The subsequent biotransformation was carried out at a starting compound (3,3,3-trifluoro-2-hydroxy-2-ethylpropionamide) concentration of 0.5% and using a cell suspension having an optical density of OD$_{650}$=10. The whole was stirred at 130 rpm and at 37° C. The biotransformation was measured by means of chiral GC and was complete after 125 h.

In order to separate the R-acid which had been formed from the S-amide, the pH of the biotransformation solution was first of all adjusted from 7.8 to 10.0 using 30% NaOH. The solution was then extracted with ethyl acetate (600 ml), after which the whole was filtered through Celite and the phases were separated. The resulting aqueous phases were adjusted to a pH of 10.0 with 30% NaOH and filtered off with ethyl acetate; the phases were then separated. The whole operation was repeated approx. 3 times. The combined extracts were dried over Na$_2$SO$_4$ and then concentrated on a rotary evaporator. The resulting oil was treated with hexane and the whole was cooled down to −18° C. After 12 h, the suspension was filtered off, washed with hexane and dried. The crude product (approx. 1.8 g) was subsequently recrystallized in hot toluene and then dried. 1.72 g of (−)-amide ($\alpha_D$=−13.2, c=3.75 in methanol) were obtained as a beige solid, corresponding to a yield of 34.4%, and having an enantiomeric excess (ee) of greater than 98%.

In order to isolate the (+)-acid ($\alpha_D$=+9.75, c=3.31 in methanol) which had been formed, the pH of the aqueous phase was adjusted from 9.4 to 1.0 using 32% HCl and extracted twice with ethyl acetate. The organic phases were combined, dried with Na$_2$SO$_4$ and then concentrated on a rotary evaporator. 15 ml of toluene were then added to the residue. After concentrating, 2.18 g of a brownish solid were obtained. After recrystallizing in hot toluene, 1.97 g of a beige solid, corresponding to a yield of 39.1% and having an ee value of 85.2%, were obtained.

The results are depicted in FIG. 1.

EXAMPLE 2

Preparation of (S)-3,3,3-trifluoro-2-amino-2-methylpropionamide

2.1 Preparation of racemic 3,3,3-trifluoro-2-amino-2-methylpropionamide

The preparation was carried out in analogy with EP-A 0 298 029.

Potassium cyanide (66.4 g) and distilled water (50 ml) were introduced initially and the suspension was cooled down to 0 to 5° C. Trifluoroacetone (112.1 g) was then added within a period of 1.5 h. The reaction mixture was transferred into a Berghof autoclave and heated to approx. 85° C. After approx. 1.5 h, ammonia solution (124.5 g) was added dropwise and the whole was heated at 110–115° C. for approx. 7 h.

The resulting brown solution was concentrated on a rotary evaporator at 60° C. in order to obtain 181.4 g of an amorphous brown mass. The product was sublimed at 140° C./0.1 mbar and then recrystallized from ethyl acetate. 0.67 g of a white solid, corresponding to a yield of 3%, was obtained.

2.2 Biotransformation

The biotransformation was carried out using a cell-free enzyme extract of *E. coli* XL-1-Blue MRF/pPRS7. For this, the cells were grown in NYB containing 100 μg of ampicillin/ml up to an optical density of $OD_{650}$=3.59. They were then washed in 100 mM phosphate buffer and subsequently resuspended in the same buffer to an $OD_{650}$ of 19. The cells were disrupted by being treated 3 times in a French press, after which the cell extract was heated at 75° C. for 5 min and the cell debris were removed by centrifugation (20 000×g). The clear supernatant had a protein concentration of 9.75 mg/ml and was used for the biotransformation. For this, 0.9 mg of enzyme extract were added, per ml, to 0.5% racemic 3,3,3-trifluoro-2-amino-2-methylpropionamide at 40° C. The reaction was monitored by means of chiral GC. The transformation was complete after 5 min.

The reaction was stopped by adding the same volume of ethyl acetate and the whole was then extracted 4 times with ethyl acetate.

In order to isolate the (S)-amide, the aqueous phase was extracted (4 times) with 200 ml of ethyl acetate and the combined extracts were dried with $NaSO_4$ and subsequently concentrated on a rotary evaporator at 40° C. 640 mg of a yellowish brown solid were obtained. This solid was recrystallized from 0.5 g of ethyl acetate and hexane (4 ml). 0.5 g of (S)-amide, corresponding to a yield of 38.5% based on the racemate employed, was obtained. The ee value was 100.

What is claimed is:

1. A process for preparing optically active 3,3,3-trifluoro-2-alkylpropionic acid derivatives of the general formulae

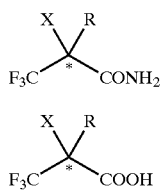

in which R denotes ethyl or methyl and X denotes —OH or $NH_2$, with the exception that, when R=methyl, X≠OH, comprising the transformation of a racemic 3,3,3-trifluoro-2-alkylpropionamide of the general formula

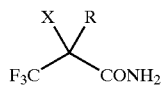

in which R and X have said meaning, either using microorganisms which are capable of utilizing the latter, as their sole source of nitrogen, in the form of the racemate or of one of its optically active isomers, or using a polypeptide which possesses amidohydrolase activity and which is capable of hydrolyzing the latter.

2. The process as claimed in claim 1, wherein the racemic 3,3,3-trifluoro-2-alkylpropionamide of the general formula

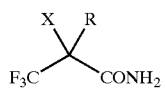

is prepared by hydrolyzing a 3,3,3-trifluoro-2-alkylpropiononitrile of the general formula

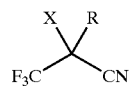

with a mineral acid.

3. The process as claimed in claim 2, characterized in that the mineral acid employed is sulfuric acid.

4. The process as claimed in claim 2, characterized in that the hydrolysis is carried out at a temperature of from 20 to 140° C.

5. The process as claimed in claim 1, characterized in that the biotransformation is carried out using microorganisms of the genus Klebsiella.

6. A process for preparing optically active 3,3,3-trifluoro-2-alkylpropionic acid derivatives of the general formula

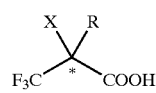

in which R denotes ethyl or methyl and X denotes —OH or $NH_2$, with the exception that, when R=methyl, X≠OH, characterized in that, in the first step, a racemic 3,3,3-trifluoro-2-alkylpropionamide of the general formula

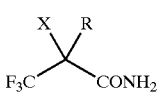

in which R and X have said meaning, is transformed, either using microorganisms which are capable of utilizing the latter, as their sole source of nitrogen, in the form of the racemate or of one of its optically active isomers, or using a polypeptide which possesses amidohydrolase activity and which is capable of hydrolyzing the latter, into an optically active 3,3,3-trifluoro-2-alkylpropionamide of the general formula

in which R and X have said meaning, and the latter is then hydrolyzed, in the second step and in a known manner, into the optically active 3,3,3-trifluoro-2-alkylpropionic acid derivative (formula II).

7. The process as claimed in claim 3, characterized in that the hydrolysis is carried out at a temperature of from 20 to 140° C.

8. A process for preparing optically active 3,3,3-trifluoro-2-alkylpropionic acid derivatives of the general formulae

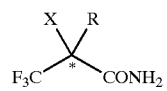

-continued

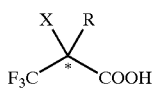
II in which R denotes ethyl or methyl and X denotes —OH or NH₂, with the exception that, when R=methyl, X≠OH, comprising the step of transforming a racemic 3,3,3-trifluoro-2-alkylpropionamide of the general formula

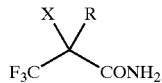
III in which R and X are defined as above, with microorganisms which are capable of using the 3,3,3-trifluoro-2-alkylpropionamide as their sole source of nitrogen, in the form of the racemate or of one of its optically active isomers.

9. A process for preparing optically active 3,3,3-trifluoro-2-alkylpropionic acid derivatives of the general formulae

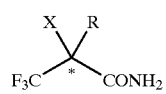
I

II in which R denotes ethyl or methyl and X denotes —OH or NH₂, with the exception that, when R=methyl, X≠OH, comprising the step of transforming a racemic 3,3,3-trifluoro-2-alkylpropionamide of the general formula

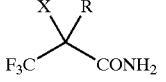
III in which R and X are defined as above, with a polypeptide which possesses amidohydrolase activity and is capable of hydrolyzing the 3,3,3-trifluoro-2-alkylpropionamide.

* * * * *